US006423707B1

(12) United States Patent
Yang et al.

(10) Patent No.: US 6,423,707 B1
(45) Date of Patent: Jul. 23, 2002

(54) NITROIMIDAZOLE ESTER ANALOGUES AND THERAPEUTIC APPLICATIONS

(75) Inventors: Li-Xi Yang; Hui-Juan Wang; Xiandao Pan, all of San Francisco, CA (US)

(73) Assignee: California Pacific Medical Center, San Francisco, CA (US)

( * ) Notice: Subject to any disclaimer, the term of this patent is extended or adjusted under 35 U.S.C. 154(b) by 0 days.

(21) Appl. No.: 09/650,027

(22) Filed: Aug. 28, 2000

(51) Int. Cl.$^7$ .................. A61K 31/54; A61K 31/47; C07D 279/36; C07D 215/00; C07D 233/02
(52) U.S. Cl. .................. 514/225.8; 514/314; 514/326; 514/397; 514/398; 544/31; 546/152; 546/245; 548/315.4; 548/327.1
(58) Field of Search .................. 548/315.4, 327.1; 514/397, 398, 225.8, 314, 326; 544/31; 546/152, 245

(56) References Cited

U.S. PATENT DOCUMENTS

| | | | |
|---|---|---|---|
| 3,997,572 A | 12/1976 | Cusic et al. | 260/281 |
| 4,160,827 A | 7/1979 | Cho et al. | 424/199 |
| 4,456,610 A | 6/1984 | Hofheinz et al. | 424/273 |
| 4,482,722 A | 11/1984 | Thorbek et al. | 548/338 |
| 5,143,934 A | 9/1992 | Lading et al. | 514/396 |
| 5,186,936 A | 2/1993 | Groves | 424/435 |
| 5,618,559 A | 4/1997 | Desai et al. | 424/468 |
| 5,618,840 A | 4/1997 | Wright | 514/549 |
| 5,629,021 A | 5/1997 | Wright | 424/489 |
| 5,693,791 A | * 12/1997 | Truett | 540/222 |
| 5,700,825 A | 12/1997 | Hofer et al. | 514/397 |
| 5,840,744 A | 11/1998 | Borgman | 514/398 |
| 6,017,516 A | 1/2000 | Mody et al. | 424/55 |

FOREIGN PATENT DOCUMENTS

| | | |
|---|---|---|
| CA | 784711 | 7/1965 |
| GB | 2076402 | 5/1981 |
| WO | 98/14190 | 4/1998 |

OTHER PUBLICATIONS

Rao et al. , 1990, Synthesis, insecticidal and antifeedant activities of new type of pyrethroid esters. Indian J. Chem., vol. 29B, pp. 1034–1040.*
Aboul–Fadl el al., 1998, Metronidazole twin ester prodrugs II. Non identical twin esters of metronidazole and some antiprotozoal halogenated hydroxyquinoline derivatives, vol. 66, pp. 309–324. Abstract.*
Peikov et al., 1995, Synthesis of some ester derivatives of theophylline in the poresence of N, N'–dicyclohexylcarbodiimide and 4–(dimethylamino)pyridine, vol. 48, pp. 29–32. Abstract.*
Baehni et al., "*Treponema denticola* Induces Actin Rearrangement and Detachment of Human Gingival Fibroblasts," *Infection and Immunity*, 60, pp. 3360–3368, 1992.
Bell et al., "Rapid Eradication of *Helicobacter pylori* Infection," *Ailment Pharmacol. Ther.*, 9, pp. 41–46, 1995.
Carmine et al., "Tinidazole in Anaerobic Infections," *Drugs*, 24, pp. 85–117, 1982.
Cellini et al., "*Helicobacter pylori*: A Fickle Germ," *Microbiol. Immunol.*, 38, pp. 25–30, 1994.
Cho et al., "Metronidazole Phosphate—A Water–Soluble Prodrug for Parenteral Solutions of Metronidazole," *Journal of Pharmaceutical Sciences*, 71, pp. 410–414, 1982.
Cho et al., "Serum–Catalyzed Hydrolysis of Metronidazole Amino Acid Esters," *Journal of Pharmaceutical Sciences*, 74, pp. 883–885, 1985.
Clyne et al., "*Helicobacter pylori* Requires and Acidic Environment to Survive in the Presence of Urea," *Infection of Immunity*, 63, pp. 1669–1673, 1995.
Corea and Miller, "*Helicobacter pylori* and Gastric Atrophy—Cancer Paradoxes," *J. National Cancer Institute*, 87, pp. 1731–1732, 1995.
Cosar et al., "Nitro–imidazoles–Préparation et activité chimiothérapeurique," *Arzeimittel–Forsch*, 16, 23–9 (Fr), 66:2512e, 1967.
Covacci et al., "Helicobacter pylori Virulence and Genetic Geography," *Science*, 284, pp. 1328–1333, 1999.

(List continued on next page.)

Primary Examiner—Mukund J. Shah
Assistant Examiner—Tamthom N. Truong
(74) Attorney, Agent, or Firm—Cooley Godward LLP

(57) ABSTRACT

Novel nitroimidazole compounds are provided that have a substituent linked via an ester linkage. The ester linkage may be obtained by derivation of the hydroxyl group of metronidazole. These nitroimidazole ester analogs have anti-microbial activity, with a number of novel compounds having an anti-microbial activity that is significantly improved with respect to metronidazole. Two particularly preferred embodiments are shown by Formulas 4 and 5 below:

FORMULA 4

FORMULA 5

36 Claims, No Drawings

OTHER PUBLICATIONS

Deshpande et al, "Rapid Large–Scale Growth of *Helicobacter pylori* in Flasks and Fermentors," *Applied & Environmental Microbiology*, 61, pp. 2431–2435, 1995.

Diker and Hascelik, "The Bactericidal Activity of Tea Against *Helicobacter pylori*," *Letters in Applied Microbiology*, 19, pp. 299–300, 1994.

Fox and Lee, "The Role of Helicobacter Species in Newly Recognized Gastrointestinal Tract Diseases of Animals," *Laboratory Animal Science*, 47, pp. 222–255, 1997.

Haas et al., "In Vivo Selection of Resistant *Helicobacter pylori*," *Antimicrobial Agents and Chemotherapy*, 34, pp. 1637–1641, 1990.

Jenks et al., "Exposure to Metronidazole In Vivo Readily Induces Resistance in *Helicobacter pylori* and Reduces the Efficacy of Eradication Therapy in Mice," *Antimicrobial Agents and Chemotherapy*, 43, pp. 777–781, 1999.

Johansen and Larsen, "A Comparison of the Chemical Stability and the Enzymatic Hydrolysis of a Series of Aliphatic and Aromtic Ester Derivatives of Metronidazole," *International Journal of Pharmaceutics*, 26, pp. 227–241, 1985.

Johansen et al., "In Vitro Evaluation of Dermal Prodrug Delivery—Transport and Bioconversion of a Series of Aliphatic Esters of Metronidazole," *International Journal of Pharmaceutics*, 32, pp. 199–206, 1986.

Kehler et al., "Evaluation of Three Commercially Available Blood Culture Systems for Cultivation of *Helicobacter pylori*," *J. Clinical Microbiol.*, 32, pp. 1597–1598, 1994.

Khulusi et al, "The Effects of Unsaturated Fatty Acids on *Helicobacter pylori* in vitro," *J. Med. Microbiol.*, 42, pp. 276–282, 195.

Kuipers et al., "*Helicobacter pylori* and Atrophic Gastritis: Importance of the cagA Status," *J. National Cancer Institute*, 87, pp. 1777–1780, 1995.

Moore et al., "Metrondazole Uptake in *Helicobacter pylori*," *Can. J. Microbiol.*, 41, pp. 746–749, 1995.

Oderda et al, "Eighteen Month Follow Up of *Helicobacter pylori* Positive Children Treated with Amoxycillin and Tinidazole," *Gut*, 33, pp. 1328–1330, 1992.

Rautelin et al., "Ribotyping Patterns and Emergence of Metronidazole Resistance in Paired Clinical Samples of *Helicobacter pylori*," *J. Clinical Microbiology*, 32, pp. 1079–1082, 1994.

Rautelin et al., "Role of Metronidazole Resistance in Therapy of *Helicobacter pylori* Infections," *Antimicrobial Agents and Chemotherapy*, 36, pp. 163–166, 1992.

Reynolds and Penn, "Characteristics of *Helicobacter pylori* Growth in a Defined medium and Determination of its Amino Acid Requirements," *Microbiology*, 140, pp. 2649–2656, 1994.

Rugge et al., "Re: *Helicobacter pylori* and Atrophic Gastritis: Importance of the cagA Status," *J. National Cancer Institute*, 88, p. 762, 1996.

Upcroft et al., "Efficacy of New 5–Nitroimidazoles against Metronidazole–Susceptible and –Resistant *Giardia, Trichomanas*, and Entamoeba spp.," *Antimicrobial Agents and Chemotherapy*, 43, pp. 73–76, 1999.

Welch and Vatne, "The Preparation and Histomonastatic Activity of Some Haloethylimidazoles," *J. Med. Chem.*, 11 (3), pp. 370–371, 1968.

Winkelmann et al., "Chemotherapeutically Active Nitro Compounds," *Arzneim.–Forsch./Drug Res.*, 27, pp. 2251–2263, 1977.

* cited by examiner ined States Patent (skipped header)

NITROIMIDAZOLE ESTER ANALOGUES AND THERAPEUTIC APPLICATIONS

STATEMENT REGARDING FEDERALLY SPONSORED RESEARCH OR DEVELOPMENT

This invention was made with Government support under Grant Agreement No. DAMD 17-99-1-9018 awarded by the United States Department of Defense. The Government has certain rights in this invention.

BACKGROUND OF THE INVENTION

1. Field of the Invention

The present invention generally relates to nitroimidazole ester analogues, such as metronidazole ester analogues, and more particularly relates to novel metronidazole ester analogues that have anti-microbial activity and therapeutic applications thereof.

2. Description of Related Art

Metronidazole and similar compounds such as tinidazole have long been known as anti-microbial compounds. For example, metronidazole is known to be useful for the treatment of various conditions, including amebiasis (acute amebic dysentery), trichomoniasis, bacterial vaginosis, and *Helicobacter pylori* infections associated with duodenal ulcer disease.

It has been estimated that a significant number of adults are infected with *H. pylon*. These persons, although infected, are typically not treated until and unless they develop painful symptoms such as associated with ulcers. However, this bacteria is implicated in two different cancers.

Only a few antibiotic agents are presently known that have any effect on *H. pylori*, and resistance to these is developing. Metronidazole is one of these.

U.S. Pat. No. 4,160,827, issued Jul. 10, 1979, inventors Cho et al., describes phosphates of metronidazole which are water soluble and said to be useful for treating those diseases for which metronidazole is known to be useful.

Cho et al., *Journal of Pharmaceutical Sciences*, 74(8), pp. 883–885, 1985, disclose amino acid esters of metronidazole with improved solubility (phenylalanine ester and histidine ester). Cho et al., *Journal of Pharmaceutical Sciences*, 71(4), pp. 410–414, 1982, describe water soluble metronidazole phosphate.

U.S. Pat. No. 4,482,722, issued November 13, 1984, inventors Thorbek et al. discloses the N,N-dimethylglycine ester of metronidazole, which has improved solubility and is said to be useful in the systemic treatment of anaerobic infection by parenteral administration.

Johansen and Larsen, *International Journal of Pharmaceutics*, 26, pp. 227–241, 1985, describe hydrolytic degradation rates of certain aliphatic and aromatic esters of metronidazole. These esters are described as prodrugs with increased water solubility (such as useful in preparing parenteral dosage forms) and said to have improved transport against different biological membranes. Johansen et al., *Interniational Journial of Pharmaceutics*, 32, pp. 199–206, 1986, similarly describe permeation studies with a series of aliphatic ester prodrugs.

Cosar et al., "Nitro-imidazoles-Préparation et activité chimio-thérapeurique," Arzeiniittel-Forsch, 16(1), 23–9 (Fr), 66:2512e, 1967, describe various esters of metronidazole and metronidazole analogs of which they report the most interesting are numbers 23 and 47 (of Tables 5 and 6). These are said to be active against *Trichomonas vaginalis* and others infectious agents. No. 47 is said to be distinguished by a weak toxicity and a good tolerance even upon prolonged administration.

Among formulations for various applications of metronidazole are those described by U.S. Pat. No. 5,840,744, issued Nov. 24, 1998, inventor Bordman, (describing a metronidazole composition that may be topically applied), and U.S. Pat. No. 6,017,516, issued Jan. 25, 2000, inventor Mody et al (describing a dental formulation including metronidazole benzoate and chlorhexydineglycanate).

Although metronidazole is one of the four antibiotics useful against bacteria, such as *H. pylori*, unfortunately some major problems have been encountered in the uses of metronidazole, such as in the treatment of *H. pylori* infections. Relapse is common and as earlier noted, various resistant strains are emerging. Accordingly, new compounds would be useful in the various therapeutic applications to which metronidazole may be put. Such new compounds could also provide efficacy against resistant strains of microbes, such as resistant *H. pylori* strains.

BRIEF SUMMARY OF THE INVENTION

In one aspect of the present invention, new nitroimidazole compounds are provided. Novel nitroimidazoles of the present invention typically have the structures generally illustrated by Formula A.

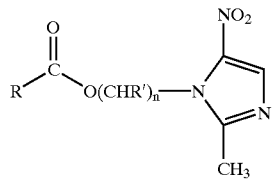

FORMULA A

In Formula A, the R moiety has at least one aromatic ring. If the at least one aromatic ring is a single phenyl bonded directly to the carbonyl carbon of the ester linkage, then it is substituted with an amide substituent, or if not an amide substituent then with at least two different substituents. If the at least one aromatic ring is not bonded directly to the carbonyl carbon of the ester linkage, and is a single phenyl, then it is substituted with at least one substituent. Preferred substituents are nitro and halogen. When the substituent is amide, then it may be primary or secondary. The at least one aromatic ring may be or include a 5 or 6 membered heterocycle, or may be multiple rings formed from all carbon atoms or including one or more of the same or different heteroatoms. Heteroatoms, when present, may be oxygen, nitrogen and/or sulfur atoms.

Further in Formula A, the R' moiety may be hydrogen, halogen, hydroxy, —SH, an alkoxy with 1–8 carbons or where one or more sulfur atoms replaces carbon, an alkyl with 1–8 carbons or where one or more sulfur atoms replaces carbon, and where n is an integer from 2 to 8.

Particularly preferred compounds are metronidazole ester analogs wherein R' is hydrogen and n is 2, as illustrated by Formula B.

FORMULA B

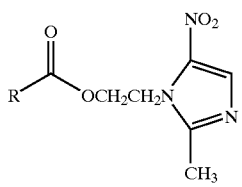

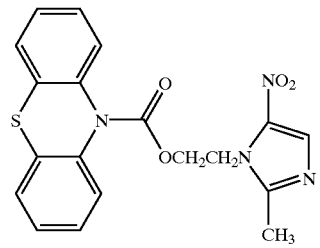

FORMULA 5C

These inventive analogs preferably have anti-microbial properties. Some of the particularly preferred embodiments have remarkable toxicity against even resistant strains of microbes, such as resistant *H pylori*. Five particularly preferred embodiments, the structures of which are shown below, have demonstrated extraordinarily potent anti-bactericidal activity in an assay with *H pylori* that is predictive of efficacy in human treatment.

FORMULA 1C

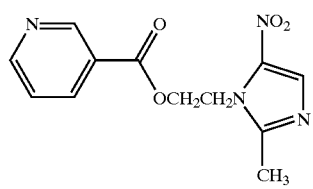

FORMULA 2C

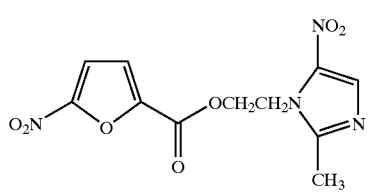

FORMULA 3C

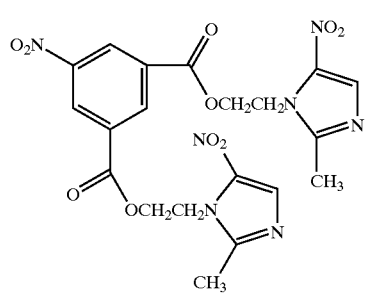

FORMULA 4C

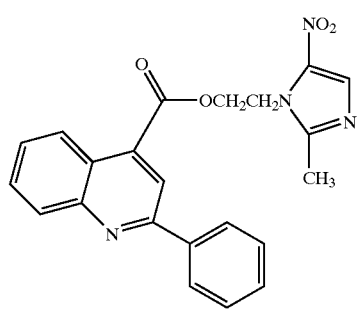

In the above-noted particularly preferred embodiments, Formula 3C is a di-ester where the at least one aromatic ring is a single phenyl bonded directly to the carbonyl carbon of the ester linkage, and is substituted with a nitro group as one substituent and with another substituent as a metronidazole ester moiety. The Formulas 1C and 2C embodiments illustrate respectively a six member heterocycle where the heteroatom is nitrogen and a five member heterocycle where the heteroatom is oxygen (and the ring is substituted with a nitro). The Formulas 4C and 5C embodiments illustrate multiple rings, where there is a phenyl substituent upon the nitrogen containing quinolyl for Formula 4C and both nitrogen and sulfur are present in the fused rings of Formula 5C.

Novel compounds of this invention are usefully formulated with pharmaceutically suitable carriers and administered for their biological activities, such as in anti-microbial applications.

DETAILED DESCRIPTION OF THE INVENTION

We have prepared a number of novel nitroimidazole compounds of the Formula A structure, shown below, and which have demonstrated anti-microbial activity. Preferred analogues of this invention have an enhanced anti-microbial activity as to at least one microbe, with respect to metronidazole. As will be hereinafter more fully described, many of the preferred embodiments have a Minimal Bactericidal Concentration (MBC) against at least one *H. pylori* strain that is less than about 25 mcg/mL and the particularly preferred five embodiments have a MBC value against a *H. pylori* resistant strain of between about 2–5 mcg/mL (by contrast to 89 mcg/mL for metronidazole). This means that these particularly preferred five embodiments are extremely potent and are about 45 times better at killing the resistant bacteria than metronidazole itself. The assay demonstrating this potency is indicative of human anti-bacterial efficacy.

Novel nitroimidazole compounds of the present invention typically have the structure generally illustrated by Formula A.

FORMULA A

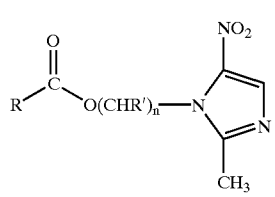

In Formula A, the R moiety includes at least one aromatic ring. If the at least one aromatic ring is a single phenyl bonded directly to the carbonyl carbon of the ester linkage, then it is substituted with an amide substituent, or if not an amide substituent then with at least two different substituents. If the at least one aromatic ring is not bonded directly to the carbonyl carbon of the ester linkage, and is a single phenyl, then it is substituted with at least one substituent. Preferred substituents are nitro and halogen. When the substituent is amide, then it may be primary, secondary, or tertiary. The at least one aromatic ring may be a 5 or 6 membered heterocycle, or maybe multiple rings formed from all carbon atoms or including one or more of the same or different heteroatoms. Heteroatoms, when present, may be oxygen, nitrogen and/or sulfur atoms.

Further in Formula A, the R' moiety may be hydrogen, halogen, hydroxy, —SH, an alkoxy with 1–8 carbons or where one or more sulfur atoms replaces carbon, an alkyl with 1–8 carbons or where one or more sulfur atoms replaces carbon, and where n is an integer from 2 to 8.

Particularly preferred compounds are metronidazole ester analogs wherein both R' and R'' are hydrogen and n is 2, as illustrated by Formula B.

FORMULA B

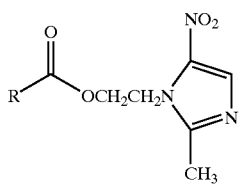

The remarkable anti-microbial activity that has been found for compounds of this invention, and the wide variations of structures possible as the R moiety of Formulas A and B, are quite surprising.

Some illustrative ring moieties for R are, e.g., pyridyl, furfuryl, quinolyl, phenothiazinyl, 9-oxo-9H-thioxanthenyl 10, 10-dioxide, chromonyl, anthraquinonyl, acetamidophenyl, quinolonyl, acridyl, benzimidazolyl, benzothiazolyl, benzopyranyl, benzoxazinyl, benzoxazolyl, pyrazinyl, phenazinyl, quinazolinyl, 1,2,3-thiadiazolyl, thiazinyl, tetrazolyl, thiazolyl, triazolyl, and triazinyl. Illustrative structures for various of these preferred R moieties are represented by embodiments of Formulas 1C–15 below, of which the Formulas 1C–5C compounds are particularly preferred.

FORMULA 1C

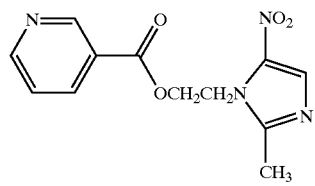

FORMULA 2C

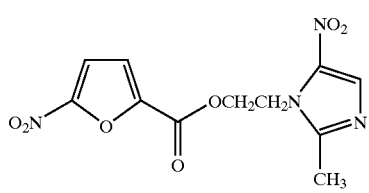

FORMULA 3C

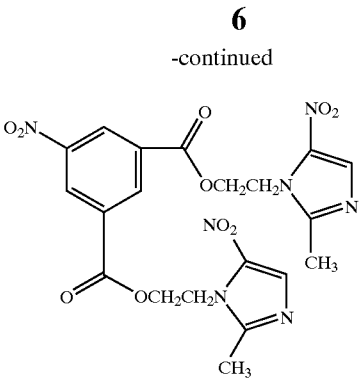

FORMULA 4C

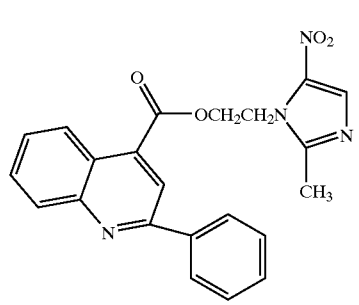

FORMULA 5C

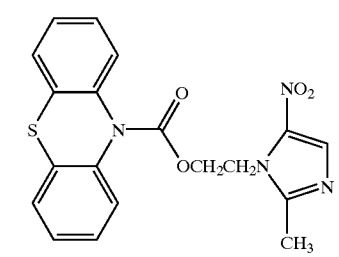

FORMULA 6

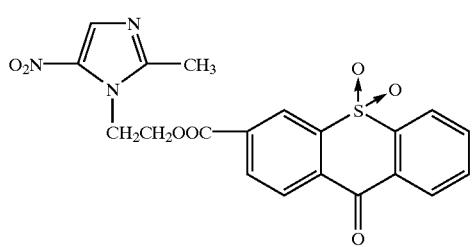

FORMULA 7

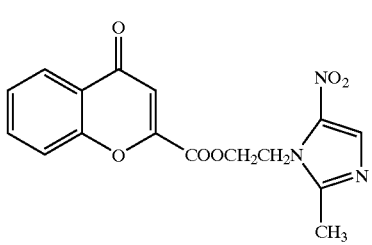

FORMULA 8

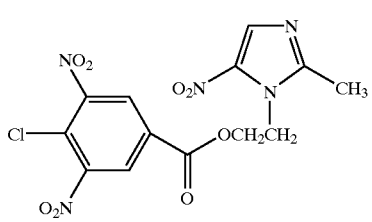

-continued

FORMULA 9

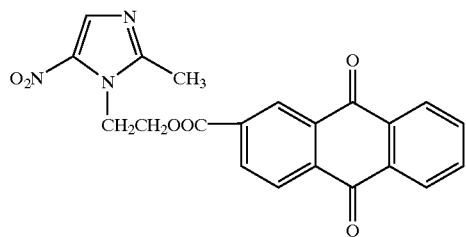

FORMULA 10

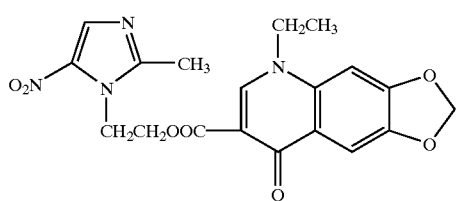

FORMULA 11

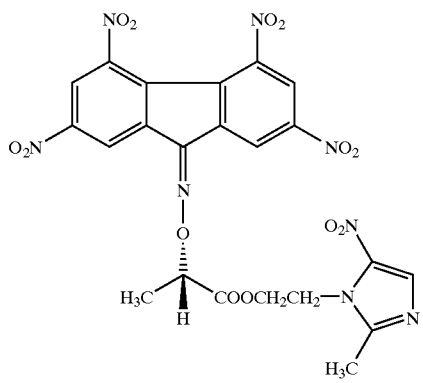

FORMULA 12

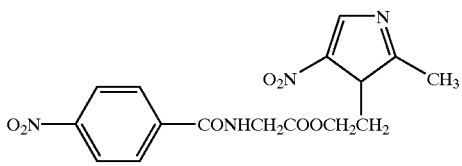

FORMULA 13

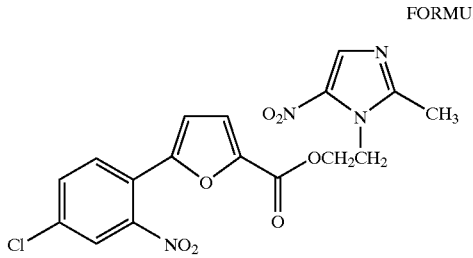

-continued

FORMULA 14

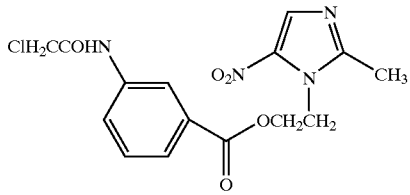

FORMULA 15

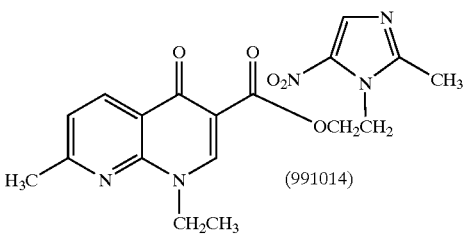

(991014)

The Formula 1C and 2C embodiments illustrate inventive compounds where the at least one aromatic ring is a single heterocyclic that is bonded directly to the carbonyl carbon while in the Formula 13 embodiment the heterocyclic is further substituted with an aromatic. The Formula 3C embodiment on one hand can be viewed as a di-ester, but when looked at in the context of Formula B, has two different sub stituents (a nitro and another met ronidazole ester moiety). The Formula 8 embodiment has the at least one aromatic ring as a phenyl that is bonded directly to the carbonyl carbon with the phenyl having two different sub stituents (neither of which is an amide). The Formula 14 embodiment, however, has an amide substituent. The Formula 4C, 5C, 6, 7 and 10 embodiments illustrate novel compounds having heterocyclics as part of multiple rings. The Formulas 4C–7 and 10 embodiments also illustrate the presence of different heteroatoms in the same or different rings and a carbonyl carbon as part of the rings, whereas the Formula 15 embodiment has two fused N-containing rings. The Formulas 9 and 11 embodiments illustrate multiple fused rings where all the ring members are carbon atoms. Formula 11, as well as Formula 12, also illustrate compounds where the at least one aromatic ring of the R substituent for Formula B is not bonded directly to the carbonyl carbon of the ester linkage. When the at least one aromatic ring is a single phenyl, then it is substituted with at least one substituent, such as the preferred nitro.

The ester linkage is believed essential for the enhanced anti-microbial activity of these metronidazole analogs. The substituent linked via the ester linkage (shown as the "R" moiety of Formulas A and B) is believed to convey an increased lipophilic character to the inventive compounds so that they have enhanced penetration into microbial membranes. Without being limited by theory, we view the R substituent as having or conveying the character of one or more an oxidizing group (quinonyl, nitro, or the like).

The novel compounds of this invention have at least one biological activity, and preferred embodiments have the at least one biological property as an anti-microbial activity, more preferably that is improved with respect to metronidazole. Metronidazole is known to have a variety of biological activities, most importantly anti-microbial activities or properties. The term "biological activity" as used herein means a property with utility in the treatment or prevention of disease or disorders affecting animals or humans, or in the regulation of an animal or human physiological condition. Among the uses known for metronidazole, to which uses compounds of this invention may be put, are in treating *H. pylori* infections, amebic dysentery, giardiasis, trichomonas vaginalis, and other parasitic diseases (e.g. clostridium difficile). The inventive compounds will be formulated in such therapeutic applications as suitable for the disease being treated, such as to be administered orally, topically, or by i.v.

For example, as demonstrated by the data of Table 1 in the experimental section, preferred embodiments are effective in killing *H. pylori* and do so with a potency a number of that is useful in treating patients having on the order of $10^6$ to about $10^7$ organisms in their gastric mucosa. Indeed, particularly preferred embodiments have substantially enhanced *H. pylori* killing effects with respect to metronidazole.

Many compounds of this invention have limited water solubility; however, drug delivery formulations are known and useful that allow materials soluble in any of water, oil, or other solutes (such as alcohol) to be formulated for delivery of drugs by any means of administration desired, such as by i.v. and i.p. Thus, for example, U.S. Pat. No. 5,629,021, issued May 13, 1997, inventor Wright, incorporated by reference, discloses micellar nanoparticles that may be formed into stable dispersions in aqueous solutions and buffers, and such nanoparticles can be used in delivering the novel compounds of this invention. Other synthetic particles suitable for administering the novel compounds, such as liposomes, nonphospholipid vesicles, and microcapsules, are also known and can be used in preparing formulations for delivering the novel metronidazole ester analogues of this invention.

Among the known formulations for delivery of biologically active agents such as metronidazole are those including oils (e.g. U.S. Pat. No. 5,143,934, issued Sep. 1, 1992) and buffering systems (e.g. U.S. Pat. No. 5,840,744, issued Nov. 24, 1998). U.S. Pat. No. 5,618,559, issued Apr. 8, 1997 discloses pharmaceutical composition with a modified-release profile for daily dosing of metronidazole.

Thus, the inventive analogues of the present invention can be prepared in formulations analogous to these various known teachings for metronidazole formulations and then be used to treat a patient, such as to treat an infection caused by a microorganism by administering a composition including an effective amount of the inventive analogue to the patient. Again, administration can be as appropriate, such as oral, topical, nasal or into the blood stream.

For one example, compositions of the present invention may be formulated as granules for oral administration which include the metronidazole ester analogues, together with various well-known tableting agents, excipients, and the like. Such tablets are contemplated for treating patients infected with a Helicobacter species, such as *Helicobacter pylori*, particularly in treating resistant species.

Alternatively, as another example, compositions of the present invention may be formulated where the novel compounds are encapsulated in synthetic particles such as liposomes, micellular nanoparticles, or nonphospholipid vesicles. Such formulations can be administered orally for treating patients infected with a Helicobacter species. Novel compounds of this invention may be incorporated into such particles, particularly for treating resistant *H. pylori*.

The clinical resolution of an infection or disease may be readily determined by a clinician of ordinary skill in the art, such as by microbiological testing or disappearance of clinically characteristic symptoms. Thus, the particular form of administration and the dosage of nitroimidazoles in accordance with this invention and/or the length of treatment may be increased or decreased based on the type of infection, the degree of susceptibility of the microorganism, the age and general health of the patient, and like factors of which a clinician of ordinary skill in the art is aware.

Further, with respect to *H. pylori*, present clinical practice frequently includes administering an anti-microbial in combination with other active ingredients, such as bismuth and amoxicillin, bismuth and tetracycline, and others. For another example, U.S. Pat. No. 5,618,840, issued Apr. 8, 1997, inventor Wright, describes an antibacterial oil-in-water emulsion that inhibits the growth of *H. pylori*, which emulsions can be administered to individuals, for example orally.

Example A gives two illustrative (prophetic) preparations of Formula A compounds. Further, compounds of this invention of Formula B may be prepared by various methods, such as by (a) the acylation of metronidazole with the corresponding organic acid chloride, or (b) the reaction of two substituents with a coupling reagent (such as DCC, EDCI, DIPC, and so on) and a catalytic agent (such as DMPA).

The following examples serve to illustrate and not to limit the present invention, where Examples 1–11 illustrate actual preparations of many of the embodiments. Examples 12 and 13 describe assays by which some of the preferred embodiments of this invention have been shown to have a particular biological activity.

The abbreviations used herein are: DCC (1,3-dicyclohexyl-carbodiimide), EDCI (1-(3-dimethylaminopropyl)-3-ethylcarbodiimide hydrochloride), DIPC (1,3-diisopropylcarbodiimide), DMAP (4-dimethylaminopyridine), and THF (tetrahydrofuran). Unless defined otherwise, all technical and scientific terms used herein have the same meaning as commonly understood by one of ordinary skill in the art to which this invention belongs.

EXAMPLE A

1. Synthesis of 1-(3-Hydroxypropyl)-2-methyl-5-nitro-1H-imidazole and its Ester

The reaction mixture of 2-methyl-5-nitroimidazole (127 g, 1.0 mol) and 1-chloro-3-hydroxypropane (500 g, 5.3 mol) will be refluxed for 24 h. Then, the excessive amount of 1-chloro-3-hydroxypropane will be removed via evaporation under a condition of 2660 Pa. To the residue, 200 ml of water will be added. The mixture will be filtered. The filtrate will be collected. The filter residue will be then rinsed with water. The water phases will be combined and alkalified with saturated sodium bicarbonate aqueous solution up to pH 9. The solution will be placed in the cold room overnight for crystallization. The crystals will be filtered, washed with water, and then dried. The crude product will be recrystallized from ethyl acetate to give 1-(3-hydroxypropyl)-2-methyl-5-nitro-1H-imidazole.

The reaction mixture of 5-nitro-2-furoic acid (157 mg, 1.0 mmol), 1-(3-hydroxypropyl)-2-methyl-5-nitroimidazole (184 mg, 1.0 mmol), EDCI (260 mg, 1.3 mmol), DMAP (10 mg, 0.1 mmol) and THF (5 ml) will be stirred at room temperature for 10 h. Evaporation of THF gives a residue which will be dissolved in ethyl acetate. The organic layer of ethyl acetate will be washed with $H_2O$, 5% $Na_2CO_3$, $H_2O$ and brine, and then dried over $MgSO_4$. The solvent will be removed under vacuum. The resulting solid will be recrystallized from $C_2H_5OH$ to give 2-methyl-5-nitro-1H-imidazole-1-propyl 5-nitro-2-furoate.

2. Synthesis of 1-(2-Hydroxybutyl)-2-methyl-5-nitro-1H-imidazole and its Ester

The reaction mixture of 2-methyl -5-nitroimidazole (127 g, 1.0 mol) and 88% formic acid will be cooled to 10° C.

under stir, then 1,2-epoxybutane (360 g, 5.0 mol) will be added dropwise to above cold solution under the condition of 10° C. After the dropping, the reactants will be placed at room temperature overnight. The formic acid will be recovered under reduced pressure. To this residue, 100 ml of water will be added. The mixture will be filtered and the filter residue will be washed with water. The water phases will be combined, alkalified with 10 M sodium hydroxide aqueous solution up to pH 9. The solution will be placed in the cold room overnight for crystallization. The crystals will be collected, washed with water, and then dried. Crude product will be recrystallized from toluene to give 1-(2-hydroxybutyl)-2-methyl-5-nitro-1H-imidazole.

The reaction mixture of 2-phenyl 4-quinolinecarboxylic acid (274 mg, 1.1 mmol), 1-(2-hydroxybutyl)-2-methyl-5-nitro-1H-imidazole (199 mg, 1.0 mmol), EDCI (228 mg, 1.2 mmol), DMAP (20 mg, 0.2 mmol) and THF (5 ml) will be stirred at room temperature for 10 h. THF will be then removed under reduced pressure. The residue will be dissolved in ethyl acetate. The organic layer will be washed with $H_2O$, 5% $Na_2CO_3$, $H_2O$ and brine, and then dried over $MgSO_4$. The solvent will be removed under reduced pressure. The resulting solid will be recrystallized from $C_2H_5OH$ to give 2-methyl-5-nitro-1H-imidazole-1-(2-hydroxybutyl) 2-phenyl-4-quinolinecarboxylate

EXAMPLE 1

2-Methyl-5-nitro-1H-imidazole-1-ethyl Nicotinate

The reaction mixture of nicotinic acid (1.23 g, 10 mmol) and thionyl chloride (3 ml) was refluxed for 2 h, the excessive thionyl chloride was evaporated under vacuum. The residue was dissolved in 5 ml of pyridine. To this solution, metronidazole (1.20 g, 7.0 mmol) was added. The mixture was stirred at 70° C. for 2 h. Pyridine was then removed under reduced pressure. The residue was dissolved in dichloromethane. The organic layer of $CH_2Cl_2$ was washed with saturated aqueous $NaHCO_3$ solution, water, and brine, and then dried over $MgSO_4$. The solvent was removed. The resulting pale yellow solid was recrystallized from ethyl alcohol to give 1.67 g (86.72%) 2-methyl-5-nitro-1H-imidazole-1-ethyl nicotinate. m.p.: 116–118° C.

The chemical structure analysis was performed by $^1$HNMR (CDCl$_3$, 600 MHz): δ9.09 (s, 1H, Pyridine-H), 8.76 (d, 1H, Pyridine-H), 8.14 (d, 1H, Pyridine-H), 7.94 (s, 1H, imidazole-H), 7.38 (m, 1H, Pyridine-H), 4.71 (d, 4H, OCH$_2$CH$_2$N), 2.49 (s, 3H, Ar—CH$_3$)

The structure of the prepared compound is shown by Formula 1C.

EXAMPLE 2

2-Methyl-5-nitro-1H-imidazole-1-ethyl 5-nitro-2-furoate

Method A. The reaction mixture of 5-Nitro-2-furoic acid (157 mg, 1.0 mmol) and thionyl chloride (2 ml) was refluxed for 2 h. The excessive thionyl chloride was evaporated under vacuum. The residue was dissolved in 4 ml of dichloromethane. To this solution, metronidazole (152 mg, 0.89 mmol) was added. After the mixture was stirred at room temperature for 20 h, water was added to this mixture. The organic layer of dichloromethane was separated, washed with 5% Na$_2$CO$_3$, H$_2$O, and brine, and then dried over MgSO$_4$. The solvent was removed, and the residue was recrystallized from C$_2$H$_5$OH—EtOAc to give 36 mg 2-methyl-5-nitro-1H-imidazole-1-ethyl 5-nitro-2-furoate. m.p.: 150–152° C.

Method B. The reaction mixture of 5-Nitro-2-furoic acid (157 mg, 1.0 mmol), metronidazole (161 mg, 0.94 mmol), EDCI (260 mg, 1.3 mmol), DMAP (10 mg, 0.1 mmol) and THF (5 ml) was stirred at room temperature for 10 h. Evaporation of THF gave a residue which was dissolved in ethyl acetate. The organic layer of ethyl acetate was washed with H$_2$O, 5% Na$_2$CO$_3$, H$_2$O and brine, and then dried over MgSO$_4$. The solvent was removed under vacuum. The resulting solid was recrystallized from C$_2$H$_5$OH to give 134 mg (44.6%) 2-methyl-5-nitro-1H-imidazole-1-ethyl 5-nitro-2-furoate. m.p.: 150–152° C.

The chemical structure analysis was performed by $^1$HNMR (CDCl$_3$, 600 MHz): δ7.98 (s, 1H, imidazole-H), 7.31 (d, 2H, furan-H), 4.75 (d, 4H, OCH$_2$CH$_2$N), 2.64(s, 3H, CH$_3$).

The structure of the prepared compound is shown by Formula 2C.

EXAMPLE 3

Di (2-methyl-5-nitro-1H-imidazole-1-ethyl) 5-nitro-1,3-benzenedicarboxylate

The reaction mixture of 5-Nitroisophthalic acid (211 mg, 1.0 mmol) and thionyl chloride (2ml) were refluxed for 2 h. The excessive thionyl chloride was evaporated under vacuum. The residue was dissolved in 6 ml of dichloromethane. To this solution, metronidazole (376 mg, 2.2 mmol) was added. The mixture solution was stirred at room temperature for 20 h. The organic layer of dichloromethane was separated, washed with 5% Na$_2$CO$_3$, H$_2$O, and brine, and then dried over MgSO$_4$. The solvent was evaporated under vacuum. The residue was recrystallized from EtOAc-THF to give 290 mg (56.09%) Di (2-methyl-5-nitro-1H-imidazole-1-ethyl) 5-nitro-1,3-benzenedicarboxylate. m.p.: 152–154° C.

The chemical structure analysis was performed by $^1$HNMR (CDCl$_3$, 600 MHz): δ8.06 (s, 2H, o-Ar-H), 8.76 (s, 1H, p-Ar-H), 7.99 (s, 2H, imidazole-H), 4.79 (m, 8H, OCH$_2$CH$_2$N), 2.54(s, 6H, CH$_3$).

The structure of the prepared compound is shown by Formula 3C.

EXAMPLE 4

2-Methyl-5-nitro-1H-imidazole-1-ethyl 2-phenyl-4-quinolinecarboxylate

Method A. The reaction mixture of 2-Phenyl-4-quinolinecarboxylic acid (249 mg, 1.0 mmol) and thionyl chloride (1.5 ml) was refluxed for 2 h. The excessive thionyl chloride was evaporated undervacuum. The residue was dissolved in 5 ml of pyridine. To this solution, metronidazole (170 mg, 0.98 mmol) was added. The mixture solution was stirred at 80° C. for 2 h. Pyridine was removed under reduced pressure. The residue was dissolved in dichloromethane. The organic layer of CH$_2$Cl$_2$ was washed with saturated aqueous NaHCO$_3$, H$_2$O, and brine, and then dried over MgSO$_4$. The solvent was removed under vacuum. The resulting yellow solid was recrystallized from CH$_3$OH-EtOAc to give 32 mg 2-methyl-5-nitro-1H-imidazole-1-ethyl2-phenyl-4-quinolinecarboxylate. m.p.: 122–124° C.

Method B. The reaction mixture of 2-Phenyl-4-quinolinecarboxylic acid (274 mg, 1.1 mmol), metronidazole (171 mg, 1.0 mmol), EDCI (228 mg, 1.2 mmol), DMAP (20 mg, 0.2 mmol) and THF (5 ml) was stirred at room temperature for 10 h. THF was then removed under reduced pressure. The residue was dissolved in ethyl acetate. The organic layer was washed with $H_2O$, 5% $Na_2CO_3$, $H_2O$, and brine, and then dried over $MgSO_4$. The solvent was removed under vacuum. The resulting solid was recrystallized from $C_2H_5OH$ to give 305 mg (76.62%) 2-methyl-5-nitro-1H-imidazole-1-ethyl 2-phenyl-4-quinolinecarboxylate. m.p.: 122–124° C.

The chemical structure analysis was performed by $^1$HNMR (CDCl$_3$, 600 MHz): δ8.55 (m, 1H, Ar—H), 8.21 (m, 4H, Ar—H), 8.04 (s, 1H, imidazole-H), 7.80 (t, 1H, Ar—H), 7.55 (m, 4H, Ar—H), 4.82 (s, 4H, OCH$_2$CH$_2$N), (s, 3H, CH$_3$)

The structure of the prepared compound is shown by Formula 4C.

EXAMPLE 5

2-Methyl-5-nitro-1H-imidazole-1-ethyl phenothiazine-10-carboxylate

A reaction mixture of phenothiazine-10-carbonyl chloride (261 mg, 1.0 mmol), metronidazole (165 mg, 0.96 mmol) and pyridine (4 ml) was heated at 90° C. for 4 h. After cooling, water was added. The mixture was filtered. The collected solid was washed with 5% aqueous $Na_2CO_3$ and $H_2O$, and then dried. The crude solid was recrystallized from EtOH to give 201 mg (53.28%) 2-methyl-5-nitro-1H-imidazole-1-ethyl phenothiazine-10-carboxylate. m.p.: 198–200° C.

The chemical structure analysis was performed by $^1$HNMR (CDCl$_3$, 600MHz): δ7.95 (s, 1H, imidazole-H), 7.21–7.3 (m, 8H, Ar—H), 4.54–4.58 (m, 4H, OCH$_2$CH$_2$N), 2.05(s, 3H, CH$_3$).

The structure of the prepared compound is shown by Formula 5C.

The compounds illustrated by Formulas 6–11 were similarly prepared, as described by Examples 6–11 below.

EXAMPLE 6

2-Methyl-5-nitro-1H-imidazole-1-ethyl 9-oxo-9H-thioxanthene-3-carboxylate

The reaction mixture of 9-oxo-9H-thioxanthene-3-carboxylic acid (288 mg, 1.0 mmol) and thionyl chloride (2 ml) was refluxed for 2 h. The excessive thionyl chloride was evaporated under the vacuum. The residue was dissolved in 3 ml of pyridine. To this solution, metronidazole (125 mg, 0.70 mmol) was added. After the mixture was stirred at room temperature for 4 h, then pyridine was removed in vacuo. The residue was dissolved in dichloromethane (50 ml). The organic layer of dichloromethane was washed with 5% $Na_2CO_3$, $H_2O$, and brine, and then dried over $MgSO_4$. The solvent was removed, and the residue was recrystallized from $C_2H_5OH$-CHCl$_3$ to give 151 mg 2-methyl-5-nitro-1H-imidazole-1-ethyl 9-oxo-9H-thioxanthene-3-carboxylate. m.p.: 128–130° C.

The chemical structure analysis was performed by $^1$HNMR (CDCl$_3$, 600 MHz): δ8.74 (s, 1H, Ar-H), 8.42 (d, 1H, Ar-H), 8.35 (d, 1H, Ar-H), 8.30 (d, 1H, Ar-H), 8.20 (d, 1H, Ar-H), 8.00 (s, 1H, imidazole-H), 7.92 (t, 1H, Ar-H), 7.84 (t, 1H, Ar-H), 4.78 (s, 4H, OCH$_2$CH$_2$N), 2.55 (s, 3H, CH$_3$).

The structure of the preferred compound is shown by Formula 6.

EXAMPLE 7

2-Methyl-5-nitro-1H-imidazole-1-ethyl 4-oxo-4H-1-benzopyran-2-carboxylate

The reaction mixture of chromone-2-carboxylic acid (190 mg, 1.0 mmol) and thionyl chloride (2 ml) was refluxed for 2 h. The excessive thionyl chloride was evaporated under vacuum. The residue was dissolved in 5 ml of dichloromethane. To this solution, metronidazole (162 mg, 0.95 mmol) was added. After the mixture was stirred at room temperature overnight some solid came out. The solid was filtered and was recrystallized from $C_2H_5OH$-CH$_3$OH to give 102 mg 2-methyl-5-nitro-1H-imidazole-1-ethyl 4-oxo-4H-1-benzopyran-2-carboxylate. m.p.: 210–212° (dec.).

The chemical structure analysis was performed by $^1$HNMR (DMSO-d$_6$, 600 MHz): δ8.10 (s, 1H, imidazole-H), 8.03 (d, 1H, Ar—H), 7.90 (t, 1H, Ar—H), 7.67 (d, 1H, Ar—H), 7.53 (t, 1H, Ar—H), 6.83 (s, 1H, Ar—H), 4.67, 4.75 (d, 4H, OCH$_2$CH$_2$N), 2.56 (s, 3H, CH$_3$)

The structure of the preferred compound is shown by Formula 7.

EXAMPLE 8

2-Methyl-5-nitro-1H-imidazole-1-ethyl 4-chloro-3,5-dinitrobenzoxylate

The reaction mixture of 4-chloro-3,5-dinitrobenzoic acid (246 mg, 1.0 mmol) and thionyl chloride (2 ml) was refluxed for 2 h. The excessive thionyl chloride was evaporated under vacuum. The residue was dissolved in 5 ml of dichloromethane. To this solution, metronidazole (162 mg, 0.95 mmol) and 0.1 ml triethylamine was added. After the mixture was stirred at room temperature for 5 h. water was added to this mixture. Dichloromethane layer was separated. The water layer was extracted with dichloromethane (20 ml×3). The organic layer of dichloromethane was washed with 5% $Na_2CO_3$, $H_2O$, and brine, and then dried over $MgSO_4$. The solvent was removed and the residue was recrystallized from ethyl acetate and petroleum ether to give 143 mg (37.1%) 2-methyl-5-nitro-1H-imidazole-1-ethyl 4-chloro-3,5-dinitrobenzoxylate. m.p.: 123–126° C.

The chemical structure analysis was performed by $^1$HNMR (CDCl$_3$, 600 MHz): δ8.51 (s, 2H, Ar—H), 7.98 (s, 1H, imidazole-H), 4.77 (s, 4H, OCH$_2$CH$_2$N), 2.53 (s, 3H, CH$_3$).

The structure of the preferred compound is shown by Formula 8.

EXAMPLE 9

2-Methyl-5-nitro-1H-imidazole-1-ethyl 9,10-dihydro-9,10-dioxo-2-anthracenecarboxylate The reaction mixture of 9,1 0-dihydro-9,10-dioxo-2-anthracenecarboxylic acid (126 mg, 0.5 mmol) and thionyl chloride (2 ml) was refluxed for 2 h. The excessive thionyl chloride was evaporated under vacuum. The residue was dissolved in 5 ml of pyridine. To this solution, metronidazole (80 mg, 0.47 mmol) was added. After the mixture was stirred at 80° C. for 2 h, water was added to this mixture. The water layer was extracted with dichloromethane (20 ml×3). The organic layer of dichloromethane was washed with 5% $Na_2CO_3$, $H_2O$, and brine, and then dried over $MgSO_4$. The solvent was removed, and the residue was recrystallized from $C_2H_5OH$—EtOAc to give 17 mg 2-methyl-5-nitro-1H-imidazole-1-ethyl 9,10-dihydro-9,10-dioxo-2-anthracenecarboxylate. m.p.: 223–225 ° (dec.).

The chemical structure analysis was performed by $^1$HNMR (DMSO-d$_6$, 600 MHz): δ7.95–8.47 (m, 8H, Ar—H and imidazole-H), 4.78(d, 4H, OCH$_2$CH$_2$N), 2.56(s, 3H, CH$_3$).

The structure of the preferred compound is shown by Formula 9.

EXAMPLE 10

2-Methyl-5-nitro-1H-imidazole-1-ethyl 1-ethyl-14-dihydro-7-methyl-4-oxo-1.8-naphthyridine-3-carboxylate The reaction mixture of nalidixic acid (232 mg, 1.0 mmol), metronidazole (171 mg, 1.0 mmol), EDCI (230 mg, 1.2 mmol), DMAP (20 mg, 0.2 mmol) and THF (5 ml) was stirred at room temperature for 24 h. THF was then removed under reduced pressure. The residue was dissolved in dichloromethane (50 ml). The organic layer was washed with $H_2O$, 5% $Na_2CO_3$, $H_2O$, and brine, and then dried over $MgSO_4$. The solvent was removed under vacuum. The resulting solid was recrystallized from $C_2H_5OH$ and ethyl acetate to give 56 mg 2-methyl-5-nitro-1H-imidazole-1-ethyl 1-ethyl-1,4-dihydro-7-methyl-4-oxo-1,8-naphthyridine-3-carboxylate. m.p.: 122–124° C.

The chemical structure analysis was performed by $^1$HNMR (CDCl$_3$, 600 MHz): δ8.63 (d, 1H, Ar—H), 8.53 (s, 1H, Ar—H), 8.00 (s, 1H, imidazole-H), 7.27 (s, 1H, Ar—H), 4.72 (d, 4H, OCH$_2$CH$_2$N), 4.48 (m, 2H, NCH$_2$), 2.67 (s, 3H, pyridine-CH$_3$), 2.64 (s, 3H, imidazole-CH$_3$), 1.49 (t, 3H, NCCH$_3$).

The structure of the preferred compound is shown by Formula 10.

EXAMPLE 11

2-Methyl-5-nitro-1H-imidazole-1-ethyl (+)-2-(2,4,5,7-tetranitro-9-fluorenylidene-aminooxy)propionate The reaction mixture of (+)-2-(2,4,5,6-tetranitro-9-fluorenylideneaminooxy)proprionic acid (223 mg, 0.5 mmol), metronidazole (86 mg, 0.5 mmol), EDCI (133 mg, 0.7 mmol), DMAP (10 mg, 0.1 mmol) and THF (5 ml) was stirred at room temperature for 6 h. THF was then removed under reduced pressure. The residue was dissolved in dichloromethane (50 ml). The organic layer was washed with $H_2O$, 5% $Na_2CO_3$, $H_2O$, and brine, and then dried over $MgSO_4$. The solvent was removed under vacuum. The resulting liquid was separated by column chromatography to give 160 mg 2-methyl-5-nitro-1H-imidazole-1-ethyl (+)-2-(2,4,5,7-tetranitro-9-fluorenylideneaminooxy)propionate.

The chemical structure analysis was performed by $^1$HNMR (CDCl$_3$, 600 MHz): δ9.49 (s, 1H, Ar—H), 8.95 (d, 2H, Ar—H), 8.89 (s, 1H, Ar—H), 7.80 (s, 1H, imidazole-H), 5.22 (t, 1H, CHO), 4.56–4.76 (m, 4H, OCH$_2$CH$_2$N), 2.53 (s, 3H, imidazole-CH$_3$), 1.80 (d, 3H, CH$_3$).

The structure of the preferred compound is shown by Formula 11.

EXAMPLE 12

A number of novel metronidazole ester analogues, including the embodiments described by Examples 1–11, were tested in the below described *Helicobacter pylori* microbicidal assay, in which the analogues were evaluated for their ability to kill 100% *H. pylori* at a given concentration.

Experimental Procedure. One hundred microliters of *Helicobacter pylon* ATCC strain 43579 working seed lot #050597 was grown in six milliliters of Brucella Broth (NOX 042099–1) in a 25 mm vented tissue culture flask. The flask was placed in an anaerobic jar using a Campy-Pak (BBL) and placed on a incubator-shaker at 37° C., 25 rpm for 72 hours. Each metronidazole analogue was weighed on an analytical balance to deliver between 1.24 mg and 2.47 mg to a clean screw capped glass specimen container. Three hundred and twenty microliters of DMSO (sigma lot #95H0655) was delivered aseptically to the glass vial and the drug was solubilized by mechanical shaking. The solution was then extracted using either a 1 cc tuberculin syringe or a 100 μL pipetteman with sterile tips and placed in 9.7 mL of Brucella broth (NOX 042099–1) in a sterile 15 mL screw capped polypropylene conical tube. Three milliliters of this solution was placed in a 25 mm vented tissue culture flask and three milliliters of an *H. pylori* working solution was delivered to the flask. Further dilutions were prepared in 25 mm vented tissue culture flasks as follows:

1 mL original drug solution mixed with 2 mL Brucella Broth 0.5 mL original drug solution mixed with 2.5 mL Brucella Broth 0.1 mL original drug solution mixed with 2.9 mL Brucella Broth 0.05 mL original drug solution mixed with 2.95 mL Brucella Broth 0.01 mL original drug solution mixed with 2.99 mL Brucella Broth The *H pylori* working solution was prepared from the 72 hour culture by delivering 1 mL to 35 mL on an incubator-shaker at 37° C., 25 rpm for 72 hours. The flasks were then evaluated for clarity. Quantitative cultures were performed in duplicate from undilute to $10^{-4}$ by adding 0.5 mL from the 25 mm flask to 4.5 mL Sterile Water for Injection (Baxter C404905) to prepare the initial 1:10 dilution. Subsequent dilutions from $10^{-2}$ to $10^4$ were prepared by adding 100 μL innoculum to 900 μL WFI. Ten microliters from each dilution was plated in duplicate on TSAII plates (BLL F2RRKN/0728) and incubated in an anaerobic jar using a Campy-Pak (BBL) and placed on an incubator-shaker at 370° C., 25 rpm for 72 hours.

Analysis of Results. The lowest concentration of the metronidazole analogue that was observed to be clear was the Minimal Inhibitory Concentration (MIC). The lowest concentration of the metronidazole analogue that killed 100% of the *H pylori* working solution was the Minimal Bactericidal concentration (MBC).

Table 1 gives the results for the Formula 1–15 embodiments on a metronidazole resistant *H. pylori* isolate (ATCC strain 43579).

TABLE 1

Effects of Novel Nitroimidazole Ester Analogues on Metronidazole-Resistant *H. Pylori* Isolate (American Type Culture Collection [ATCC] Strain 43579).

| Compounds | Innoculum (CFU) | MBC (mcg/mL) | Bactericidal Activity Index |
|---|---|---|---|
| Positive Control | 4,000,000 | 89 mcg/mL | 1 |
| Inventive Embodiments | | | |
| Formula 1C | 9,000,000 | 5 | 17.8 |
| Formula 2C | 1,000,000 | 3 | 29.7 |
| Formula 3C | 1,000,000 | 3 | 29.7 |
| Formula 4C | 3,000,000 | 2 | 45 |
| Formula 5C | 1,000,000 | 2 | 44.5 |
| Formula 6 | 5,000,000 | 14 | 6.4 |
| Formula 7 | 9,000,000 | 10 | 8.9 |
| Formula 8 | 1,000,000 | 63 | 1.4 |
| Formula 9 | 5,000,000 | 12 | 7.4 |
| Formula 10 | 7,000,000 | 7 | 12.7 |
| Formula 11 | 1,000,000 | 17 | 5.2 |
| Formula 12 | 1,000,000 | 85 | 1 |
| Formula 13 | 9,000,000 | >97 | |

TABLE 1-continued

Effects of Novel Nitroimidazole Ester Analogues on Metronidazole-Resistant *H. Pylori* Isolate (American Type Culture Collection [ATCC] Strain 43579).

| Compounds | Innoculum (CFU) | MBC (mcg/mL) | Bactericidal Activity Index |
|---|---|---|---|
| Formula 14 | 1,000,000 | 10 | 6.0 |
| Formula 15 | 1,000,000 | 15 | 8.9 |

As seen by the above data, the compounds of Formulas 4C and 5C had a remarkable bactericidal activity with only 2 mcg/mL needed to kill 100% of the *H. pylori* strain in working solution. The next best inventive compounds in this assay were Formulas 2C and 3C, so that only 3 mcg/mL killed 100% of the *H. pylori* strain in working solution. Formulas 1C and 10 were also quite potent with only 4 and 7, respectively, mcg/mL to kill 100% of the *H pylori* strain in working solution. As seen from the innoculum column, the number killed correspond to the range of $10^6$ to about $10^7$ organisms in the gastric mucosa of infected persons.

The *H. pylori* microbicidal assay was repeated for the Formula 4C and 5C compounds, but with another *H pylori* isolate (a virulent human isolate used in the germ-free pig model). These preferred embodiments were shown potent in killing the isolate (a MBC of 10.25 mcg/mL), which shows that their antimicrobial activity was not strain specific.

Preferred embodiments of the invention have a MBC with *H. pylori* ATCC strain 43579 of about 25 mcg/mL or less. But even the compounds of Formulas 8, 12 and 13 tested at less than, or only slightly greater than, the MBC of the metronidazole control, and it should be recalled that metronidazole is only one of a small handful of antibiotics that presently have any effect on this bacteria in treating humans.

EXAMPLE 13

Five novel metronidazole ester analogues were upscaled to 1 gram production lots and tested in the *Helicobactor pylori* microbicidal assay. The analogues were evaluated for their ability to kill 100% *H. pylori* at a given concentration. The analogues that were tested were Formulas 1C–5C.

Experimental Procedure: One hundred microliters of *Helicobactor pylori* ATCC strain 43579 working seek lot #050597 and Ohio State university *Helicobactor pylori* isolate working seed lot #061697 were grown in 6 ml of Brucella Broth (NOX 082599-1) in a 25-mm vented tissue culture flask (COSTAR). The flask was placed in an anaerobic jar using a Campy-Pak (BBL) and placed on an incubator-shaker (New Brunswick) at 37° C., 25 rpm for 72 hours. Each mitronidazole analogue was weighed on an analytical balance to deliver between 1.9 mg and 1.52 mg to a clean screw capped glass specimen container. 320 ml of DMSO (Sigma lot #95H0655) was delivered aseptically to the glass vial and the drug was solubilized by mechanical shaking. The solution was then extracted using either a 1 cc tuberculin syringe or a 100 μL pipettman with sterile tips and placed in 9.7 mL of Brucella Broth (NOX 082599-1) in a sterile 15 mL screw capped polypropylene conical tube. 3 ml of this solution was placed in each of two 25-mm vented tissue culture flask (COSTAR) and 3 ml of each *H pylori* working solution was delivered to one of the flasks. Further dilutions were prepared in duplicate in 25-mm vented tissue culture flasks as follows:

1 mL original drug solution mixed with 2 mL Brucella Broth 0.5 mL original drug solution mixed with 2.5 mL Brucella Broth 0.1 mL original drug solution mixed with 2.9 mL Brucella Broth 0.05 mL original drug solution mixed with 2.95 mL Brucella Broth 0.01 mL original drug solution mixed with 2.99 mL Brucella Broth The *H. pylori* working solution was prepared from the 72 hour culture by delivering 1 mL to 35 mL Brucella Broth. Each drug solution was placed in an anaerobic jar using a Campy-Pak (BBL) and placed on an incubator-shaker (New Brunswick) at 37° C., 25 rpm for 72 hours. The flasks were then evaluated for clarity.

Quantitative cultures were performed in cuplicate from undiluted to $10^{-4}$ by adding 0.5 mL from the 25-mm flask to 4.5 mL sterile water for irrigation (Baxter G957134) to prepare the initial 1:10 dilution. Subsequent dilutions from $10^{-2}$ to $10^{-4}$ were prepared by adding 100 μL innoculum to 900 μL water. 10 mL from each dilution was plated in duplicate on TSAII plates (BBL 0126327) and incubated in an anaerobic jar using a Campy-Pak (BBL) and placed on an incutbator-shaker (New Brunswick) at 37° C., 25 rpm for 72 hours.

Analysis of Results: The lowest concentration of the metronidazole analogue that was observed to be clear was the Minimal Inhibitory Concentration (MIC). The lowest concentration of the metronidazole analogue that killed 100% of the *H. pylori* working solution was the Minimal Bactericidal Concentration (MBC).

Table 2 gives the results for the Formulas 1–5 embodiments on two strains of *H pylori* isolates.

TABLE 2

Comparative Evaluation of Five Promising Nitroimidazole Ester Analogues on Two Strains of *H. Pylori* Isolates

| Compound | Innoculum (CFU) | MBC (mcg/mL) OSU Isolate 061697 | MBC (mcg/ml) *H. Pylori* 43579 |
|---|---|---|---|
| Formula 1C | 3,000,000 | 22.3 | 22.3 |
| Formula 2C | 3,000,000 | 12.6 | 12.6 |
| Formula 3C | 3,000,000 | 19.8 | 19.8 |
| Formula 4C | 5,000,000 | 20.5 | 10.3 |
| Formula 5C | 5,000,000 | 10.3 | 10.3 |

It is to be understood that while the invention has been described above in conjunction with preferred specific embodiments, the description and examples are intended to illustrate and not limit the scope of the invention, which is defined by the scope of the appended claims.

It is claimed:

1. A compound having the structure illustrated by Formula 1A

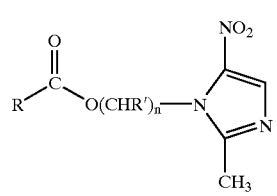

FORMULA 1A wherein (1) R is a pyridine moiety, (2) R' is hydrogen, halogen, hydroxy, —SH, alkoxy of 1–8 carbons, or alkylthio of 1–8 carbons; and (3) n is an integer from 2 to 8.

2. The compound of claim 1 having the structure illustrated by Formula 1B

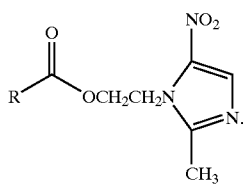

FORMULA 1B

3. The compound of claim 2 having the structure illustrated by Formula 1C

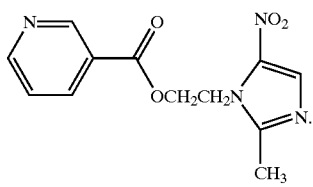

FORMULA 1C

4. A compound having the structure illustrated by Formula 2A

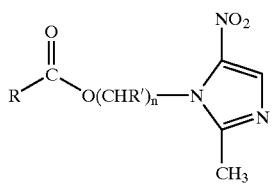

FORMULA 2A wherein (1) R is a furane moiety; (2) R' is hydrogen, halogen, hydroxy, —SH, alkoxy of 1–8 carbons, or alkylthio of 1–8 carbons; and (3) n is an integer of 2–8.

5. The compound of claim 4 having the structure illustrated by Formula 2B

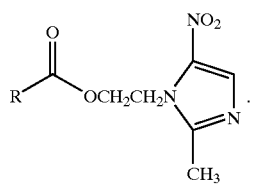

FORMULA 2B

6. The compound of claim 5 having the structure illustrated by Formula 2C

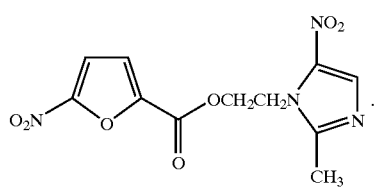

FORMULA 2C

7. A compound having the structure illustrated by Formula 3A

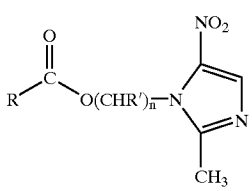

FORMULA 3A wherein (1) R is phenyl meta-substituted with a moiety having the structure

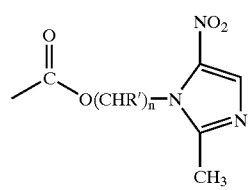

and
(2) R' is hydrogen, halogen, hydroxy, —SH, alkoxy of 1–8 carbons, or alkylthio of 1–8 carbons; and (3) n is an integer from 2 to 8.

8. The compound of claim 7 having the structure illustrated by Formula 3B

FORMULA 3B

9. The compound of claim 8 having the structure illustrated by Formula 3C

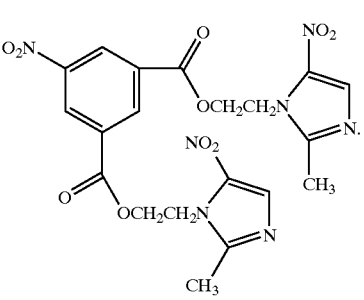

FORMULA 3C

10. A compound having the structure illustrated by Formula 4A

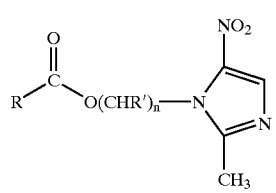

FORMULA 4A wherein (1) R is a quinoline moiety; (2) R' is hydrogen, halogen, hydroxy, —SH, alkoxy of 1–8 carbons, or alkylthio with 1–8 carbons; and (3) n is an integer from 2 to 8.

11. The compound of claim 10 having the structure illustrated by Formula 4B

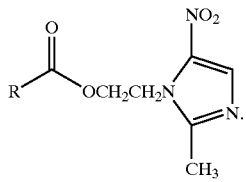

FORMULA 4B

12. The compound of claim 11 having the structure illustrated by Formula 4C

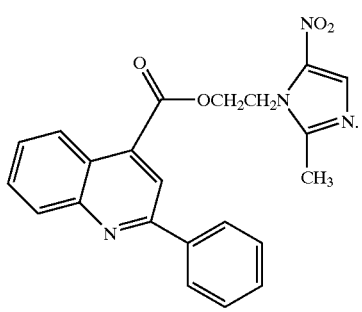

FORMULA 4C

13. A compound having the structure illustrated by Formula 5A

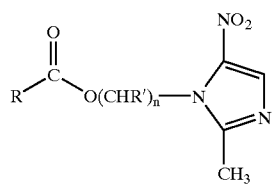

FORMULA 5A wherein (1) R is a phenothiazine moiety; (2) R' is hydrogen, halogen, hydroxy, —SH, alkoxy with 1–8 carbons, or alkylthio with 1–8 carbons; and (3) n is an integer from 2 to 8.

14. The compound of claim 13 having the structure illustrated by Formula 5B

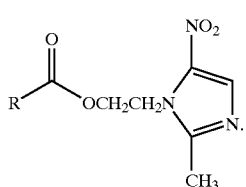

FORMULA 5B

15. The compound of claim 14 having the structure illustrated by Formula 5C

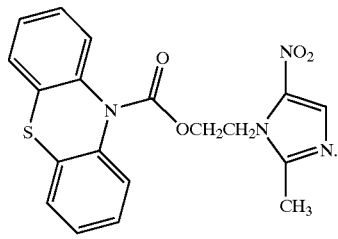

FORMULA 5C

16. An anti-microbial composition comprising:
(a) a compound with the structure illustrated by Formula A

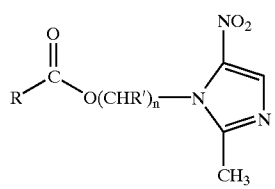

FORMULA A wherein (1) the R moiety is a pyridine moiety, a furane moiety, a quinoline moiety, a phenothiazine moiety, or a phenyl moiety meta-substituted with a moiety having the structure

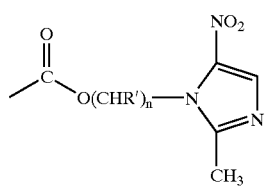

(2) R' is hydrogen, halogen, hydroxy, —SH, alkoxy of 1–8 carbons, or alkylthio of 1–8 carbons; and (3) n is an integer from 2 to 8, and (b) a pharmaceutically acceptable carrier.

17. The anti-microbial composition of claim 16, wherein the compound exhibits the structure illustrated by Formula B

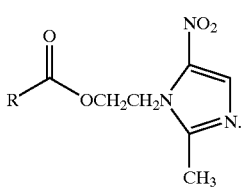

FORMULA B

18. The composition as in claim 16, wherein the carrier includes an oil.

19. The composition as in claim 16, wherein the carrier includes a tableting agent.

20. The composition as in claim 16, wherein the anti-microbial activity is determined with *H. pylori* ATCC strain 43579.

21. The composition as in claim 20, wherein the compound has a minimal bactericidal concentration of about 25 micrograms/milliliter or less.

22. The composition as in claim 16, wherein the carrier includes micellar nanoparticles.

23. The composition as in claim 16, wherein the carrier includes synthetic particles.

24. composition of claim 17, wherein the compound has the structure illustrated by Formula 1C

FORMULA 1C

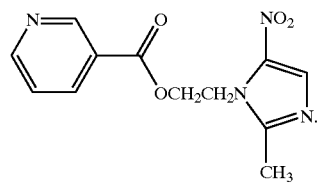

25. The composition of claim 17, wherein the compound has the structure illustrated by Formula 2C

FORMUAL 2C

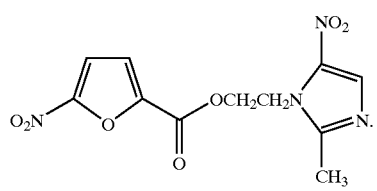

26. The composition of claim 17, wherein the compound has the structure illustrated by Formula 3C

FORMULA 3C

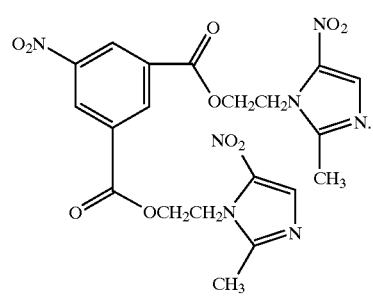

27. The composition of claim 17, wherein the compound has the structure illustrated by Formula 4C

FORMULA 4C

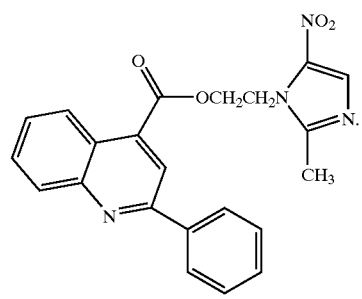

28. The composition of claim 17, wherein the compound has the structure illustrated by Formula 5C

FORMULA 5C

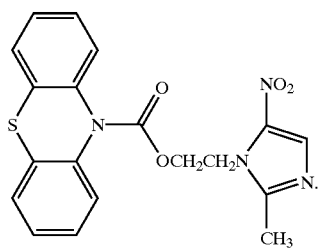

29. A method for treating or preventing the growth of *Helicobacter pylori* in a mammal, which method comprises:

administering an anti-microbial dose of a compound with the structure illustrated by Formula A

FORMULA A

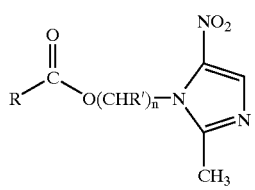

wherein (1) the R moiety is a pyridine moiety, a furane moiety, a quinoline moiety, a phenothiazine moiety, or a phenyl moiety meta-substituted with a moiety having the structure

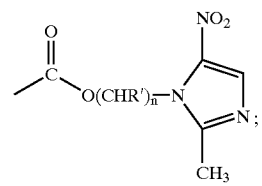

(2) R' is hydrogen, halogen, hydroxy, —SH, alkoxy of 1–8 carbons, or alkylthio of 1–8 carbons; and (3) n is an integer from 2 to 8.

30. The method of claim 29, wherein the compound exhibits the structure illustrated by Formula B

FORMULA B

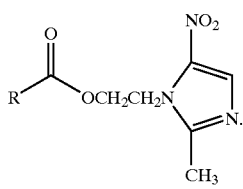

31. The method of claim 29, wherein the compound administered has an anti-microbial activity determinable with respect to *H. pylori* ATCC strain 43579.

32. The method of claim 30, wherein the compound has the structure illustrated by Formula 1C

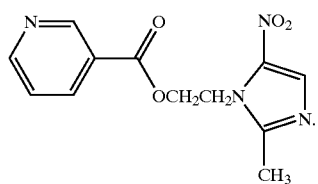

FORMULA 1C

33. The method of claim 30, wherein the compound has the structure illustrated by Formula 2C

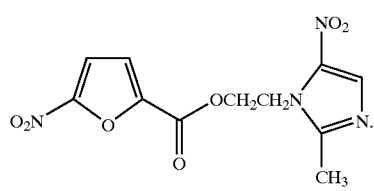

FORMUAL 2C

34. The method of claim 30, wherein the compound has the structure illustrated by Formula 3C

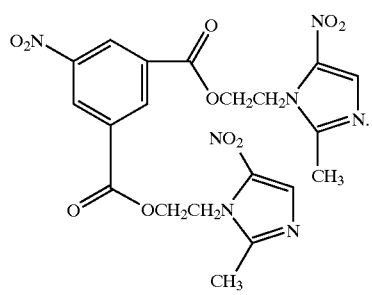

FORMULA 3C

35. The method of claim 30, wherein the compound has the structure illustrated by Formula 4C

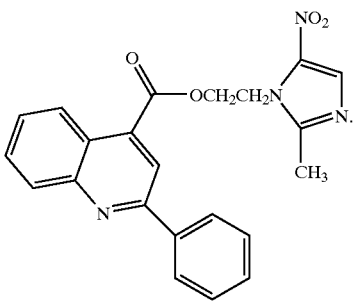

FORMULA 4C

36. The method of claim 30, wherein the compound has the structure illustrated by Formula 5C

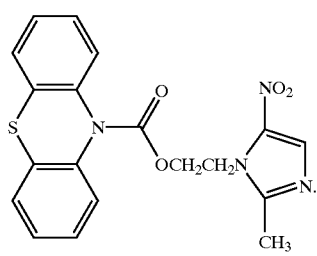

FORMULA 5C

* * * * *